United States Patent
Binder et al.

(10) Patent No.: US 6,673,945 B2
(45) Date of Patent: Jan. 6, 2004

(54) PROCESS FOR PRODUCTION OF HIGH PURITY TOCOPHEROLS

(75) Inventors: Thomas P. Binder, Decatur, IL (US); Ahmad K. Hilaly, Springfield, IL (US)

(73) Assignee: Archer-Daniels Midland Company, Decatur, IL (US)

( * ) Notice: Subject to any disclaimer, the term of this patent is extended or adjusted under 35 U.S.C. 154(b) by 0 days.

(21) Appl. No.: 10/285,700

(22) Filed: Nov. 1, 2002

(65) Prior Publication Data

US 2003/0130526 A1 Jul. 10, 2003

Related U.S. Application Data

(60) Provisional application No. 60/331,106, filed on Nov. 8, 2001.

(51) Int. Cl.[7] .............................................. C07D 311/72
(52) U.S. Cl. ......................................... 549/413; 203/41
(58) Field of Search ............................ 549/413; 203/41

(56) References Cited

U.S. PATENT DOCUMENTS

| | | | |
|---|---|---|---|
| 3,402,182 A | * | 9/1968 | Shizumasa et al. |
| 4,122,094 A | * | 10/1978 | Woziwodzki |
| 4,480,108 A | | 10/1984 | Foster |
| 5,487,817 A | * | 1/1996 | Fizet |
| 5,504,220 A | | 4/1996 | Kuo et al. |
| 5,512,691 A | * | 4/1996 | Barnicki et al. |
| 5,786,491 A | | 7/1998 | Hamlin et al. |
| 2002/0042527 A1 | | 4/2002 | Summer, Jr. |
| 2002/0142083 A1 | | 10/2002 | Jacobs |

FOREIGN PATENT DOCUMENTS

| | | |
|---|---|---|
| GB | 2 090 836 A | 7/1982 |
| JP | 60-109586 A | 6/1985 |
| JP | 60-149582 A | 8/1985 |
| JP | 1-284335 A | 11/1989 |
| WO | WO 97/07113 A1 | 2/1997 |
| WO | WO 98/24779 A1 | 6/1998 |
| WO | WO 00/43095 A2 | 7/2000 |
| WO | WO 00/43095 A3 | 9/2000 |
| WO | WO 02/50054 A2 | 6/2002 |

OTHER PUBLICATIONS

Pending–Non–Provisional United States Patent Application No. 10/246,760, Bartok, et al., filed Sep. 19, 2002, (Not Published).

Nisshin Flour Milling Co., Ltd., "Purification of tocopherols," Chem Abstracts 106:362, Abs. No. 90185s, Chemical Abstracts Service (1987).

English language abstract for Document AN1, Japanese Patent Publication No. JP 60–149582 A, published Aug. 7, 1985, Japan Patent Office (1985).

Kobashi, T., and Nishida, R., "Separation of tocopherols," Chem. Abstracts 113:135, Abs. No. 26316j, Chemical Abstracts Service (1990).

* cited by examiner

Primary Examiner—Taofiq Solola
(74) Attorney, Agent, or Firm—Sterne, Kessler, Goldstein & Fox P.L.L.C.

(57) ABSTRACT

This invention provides a method of separating tocopherols by using a weakly basic polyvinyl pyridine resin. The resin has the capacity to selectively bind tocopherols, allowing other impurities typically found in a tocopherol production plant stream to separate from the tocopherols. After loading a tocopherol-containing mixture onto a separatory column packed with the resin, the loaded column is eluted with a solvent followed by an alcohol. The eluate is collected in fractions, and the tocopherol-containing fractions are combined and concentrated to yield a purified tocopherol composition. It has been found that the present invention produces highly purified tocopherol compositions (90+%), and is particularly useful for preparing highly purified tocopherol compositions, specifically enriched in α-tocopherol.

15 Claims, No Drawings

PROCESS FOR PRODUCTION OF HIGH PURITY TOCOPHEROLS

CROSS REFERENCE TO RELATED APPLICATION

This application claims the benefit of priority of Provisional Application No. 60/331,106, filed Nov. 8, 2001.

BACKGROUND OF THE INVENTION

Background Art

Tocopherols are antioxidants and constitute the different forms of vitamin E. There are four principal homologues of tocopherols, namely, alpha (a), beta, gamma, and delta tocopherols. Although all four homologues of vitamin E exhibit activity, α-tocopherol possesses the highest biological activity.

As a class of compounds, the tocopherols have been extensively studied. Through the findings of these studies, certain biological activities have been attributed to the tocopherols. Most notably, tocopherols possess strong antioxidant properties. Tocopherols function exquisitely in their ability to remove free radicals. Thus, tocopherols find a wide range of uses in a large variety of consumer products including foodstuffs and cosmetics.

There are several methods reported in the literature for isolating tocopherols from natural sources such as vegetable oils. Tocopherols can be separated by a series of distillation steps (U.S. Pat. Nos. 5,512,691 and 5,487,817). Liquid chromatography has also been employed to fractionate tocopherols (U.S. Pat. Nos. 3,402,182 and 4,122,094). Researchers have also utilized super-critical carbon dioxide to concentrate tocopherols (JP 60149582). However, all these reported processes suffer from technical drawbacks such as the requirement of toxic chlorinated solvents, special apparatus, large volumes of eluents, and/or acidic elution steps. Also, the maximum purity of tocopherols obtainable in these processes is relatively low (about 80–90%). Therefore, there is a need for an effective separation process for large scale production of more highly purified tocopherol compositions. It is even more desirable to produce highly purified preparations of α-tocopherol.

BRIEF SUMMARY OF THE INVENTION

This invention provides a method of separating tocopherols by using a weakly basic polyvinyl pyridine resin. The resin has the capacity to selectively bind tocopherols, allowing other impurities typically found in a tocopherol production plant stream to separate from the tocopherols. After loading a tocopherol-containing mixture onto a separatory column packed with the resin, the loaded column is eluted with a solvent followed by an alcohol. The eluate is collected in fractions, and the tocopherol-containing fractions are combined and concentrated to yield a purified tocopherol composition. It has been found that the present invention produces highly purified tocopherol compositions, and is particularly useful for preparing highly purified tocopherol compositions, specifically enriched in α-tocopherol.

DETAILED DESCRIPTION OF THE INVENTION

It has been found that a purified tocopherol composition can be prepared from a tocopherol-containing mixture by eluting the mixture through a separatory column packed with a polyvinyl pyridine resin. This method provides for a more purified tocopherol product than is available through known distillation, liquid chromatography and super-critical carbon dioxide extraction processes. The method of the present invention utilizes relatively innocus chemicals and does not require complex or specialized equipment. Thus, the process of the present invention may also allow for more economical production of tocopherols.

The present invention is directed to a method for preparing an enriched α-tocopherol composition comprising:
  i. providing a tocopherol-containing mixture wherein α-tocopherol is present,
  ii. placing the tocopherol-containing mixture onto a separatory column containing a polyvinyl pyridine resin,
  iii. eluting tocopherols by washing the column with an organic solvent followed by an alcohol,
  iv. collecting the eluate in fractions,
  v. combining the fractions containing tocopherols, and
  vi. concentrating the combined fractions to prepare a purified tocopherol composition enriched in α-tocopherol.

In a preferred embodiment, the tocopherol-containing mixture is diluted with an organic solvent prior to adding to the column. Preferably, the ratio by volume of the tocopherol-containing mixture to the organic solvent is between about 1:0.5 to about 1:4. Most preferably, the ratio is about 1:2.

Any suitable solvent can be used in accordance with the present invention. Most preferably, the solvent is heptane or hexane.

It is envisioned that any suitable alcohol can be used in accordance with the present invention. In a more preferred embodiment, the alcohol is isopropanol, ethanol or methanol.

The flowrate of the solvent and the alcohol through the column can be adjusted independently to achieve maximum separation of the tocopherol from any impurities. Preferably, the flowrate of the solvent and the alcohol is between about 5 ml/min to 10 ml/min. More preferably, the flowrate for each is between about 8 ml/min to 9 ml/min.

The method of the present invention typically yields highly purified tocopherol compositions. Preferably, the α-tocopherol content is between about 90 to 100% α-tocopherol. Most preferably, the purified tocopherol composition comprises between about 95 to 100% α-tocopherol.

The following examples demonstrate the efficacy of the method of the present invention for preparing a highly purified tocopherol composition. The tocopherol compositions produced by this method are comprised of at least 90% total tocopherols. Typically the alpha form comprises at least 95% of the total tocopherols in the product.

Generally, tocopherols are derived from vegetable oils, and produced in tocopherol production plants. The product stream from such plants may contain numerous impurities. As the examples illustrate, the present method can purify a typical tocopherol-containing admixture (ATD) produced from a large-scale tocopherol production plant.

This invention utilizes a weakly basic ion exchange resin. Preferably, the weakly basic resin contains pyridine functionality. More preferably, the resin is a polymer containing 2-vinylpyridine or 4-vinylpyridine functionality with suitable cross-linking agents, such as, divinylbenzene. The degree of cross-linking is 2–52%. Illustrative examples of this weakly basic resin are Reillex HP poly-4-vinylpyridine and poly-2-vinylpyridine resins (Reilly Industries, Indianapolis, Ind., USA).

The chemicals used in the following examples are standard ACS grade chemicals.

EXAMPLE 1

A batch test was carried out in a column containing 110 ml of a polyvinyl pyridine resin (Reilly PVP-HP). The resin bed was rinsed with 100 ml of isopropanol (IPA) followed by 100 ml of heptane. The starting feed material was prepared by diluting ATD (a stream from ADM tocopherol plant) 1:2 (by volume) with heptane. About 4 ml of the feed material was added to the top of the column. The column was eluted with heptane followed by IPA. The solvents were added to the column at a flowrate of 8.2 ml/min, and different fractions were collected. The results are shown below.

|  | Feed | Fraction 1 | Fraction 2 |
|---|---|---|---|
| Total tocopherols (%) | 89.4 | 56.3 | 97.5 |
| Alpha tocopherol (% of total tocopherol) | 98 | 99.9 | 98 |
| Eluent |  | 100 ml heptane | 50 ml heptane followed by 150 ml IPA |

The purity of total tocopherols in fraction 2 was 97.5%. The alpha tocopherol content in fraction 1 was 99.9%. Therefore, this method yields purified tocopherol product fractions containing a high percentage of alpha tocopherol.

EXAMPLE 2

In this experiment, methanol was used instead of IPA. The test was carried out in a column containing 140 ml of a polyvinyl pyridine resin (Reilly PVP-HP). The resin bed was rinsed with 200 ml of IPA followed by 200 ml of heptane. The starting feed material was prepared by diluting ATD (a stream from ADM tocopherol plant) 1:2 (by volume) with heptane. About 20 ml of the feed material was added to the top of the column. The column was eluted with heptane followed by methanol. The solvents were added to the column at a flowrate of 8.4 ml/min, and different fractions were collected. The results are shown below.

|  | Feed | Fraction 1 | Fraction 2 |
|---|---|---|---|
| Total tocopherols (%) | 90.9 | 85.4 | 99.3 |
| Alpha tocopherol (% of total tocopherol) | 97.2 | 99 | 92 |
| Eluent |  | 275 ml heptane | 375 ml methanol |

As evident from the result, the purity of total tocopherols in fraction 2 was 99.3%.

EXAMPLE 3

The experiment described in example 2 was repeated with a greater amount of feed loaded on the column. About 100 ml of the feed material was added to the top of the column. The column was then eluted with heptane followed by methanol. The results are shown below.

|  | Feed | Fraction 1 | Fraction 2 |
|---|---|---|---|
| Total tocopherols | 90.9 | 85.8 | 99.3 |
| Alpha tocopherol (%) (% of total tocopherol) | 97.2 | 98 | 90 |
| Eluent |  | 250 ml heptane | 350 ml methane |

The results show the purity of total tocopherols was 99.3% in fraction 2.

EXAMPLE 4

A batch test similar to that described in Example 3 was carried out with three eluents: pure heptane (solvent 1), a mixture consisting of 96% heptane and 4% methanol (solvent 2), and pure methanol (solvent 3). The test was conducted in a column containing 160 ml of a polyvinyl pyridine resin (Reilly PVP-HP). The resin bed was rinsed with 200 ml of IPA followed by 200 ml of heptane. The starting feed material was prepared by diluting ATD (a stream from ADM tocopherol plant) 1:2 (by volume) with heptane. About 40 ml of the feed material was added to the top of the column. The column was eluted with solvent 1, followed by solvent 2, followed by solvent 3. The solvents were added to the column at a flowrate of 7.2 ml/min, and different fractions were collected. The results are shown below.

|  | Feed | Fraction 1 | Fraction 2 | Fraction 3 | Fraction 4 |
|---|---|---|---|---|---|
| Total tocopherols (%) | 92.7 | 87.2 | 96.2 | 92.9 | 96.7 |
| Alpha tocopherol (% of total tocopherol) | 97.5 | 99 | 99 | 98.7 | 89 |
| Eluent |  | 125 ml heptane | 125 ml heptane | 200 ml of mixture (96% heptane, 4% methanol) | 125 ml methanol |

The results in the above table show that the purity of total tocopherols in each of fraction 2 and fraction 4 was greater than 96%. Ninety-nine percent of the tocopherols in fraction 2 were in the alpha form.

EXAMPLE 5

In this experiment, a different starting feed material was used. The test was carried out in a column containing 200 ml of a polyvinyl pyridine resin (Reilly PVP-HP). The resin bed was rinsed with 200 ml of IPA followed by 200 ml of heptane. The starting feed material was prepared by diluting B22WW (a stream from ADM tocopherol plant) 1:2 (by volume) with heptane. About 6 ml of the feed material was added to the top of the column. The column was eluted with heptane followed by isopropanol (IPA). The solvents were added to the column at a flowrate of 8.6 ml/min, and different fractions were collected. The results are shown below.

|  | Feed | Fraction 1 | Fraction 2 |
|---|---|---|---|
| Total tocopherols (%) | 85.9 | 46.9 | 98.3 |
| Alpha tocopherol (% of total tocopherol) | 98 | 99.1 | 98.4 |
| Eluent |  | 240 ml heptane | 500 ml IPA |

As evident from the result, 99.1% of the tocopherols in fraction 1 were in the alpha form. Also, the purity of total tocopherols in fraction 2 was 98.3%.

EXAMPLE 6

The test described in Example 5 was repeated with higher loading of feed on the column. About 12 ml of the feed material was added to the top of the column, and the column was eluted with heptane followed by isopropanol (IPA). The results are shown below.

|  | Feed | Fraction 1 | Fraction 2 |
|---|---|---|---|
| Total tocopherols (%) | 84.8 | 67.8 | 96.3 |
| Alpha tocopherol (% of total tocopherol) | 98 | 100 | 98 |
| Eluent |  | 240 ml heptane | 500 ml IPA |

The results indicate that 100% of the tocopherols in fraction 1 was in the, alpha form. Also, the purity of total tocopherols in fraction 2 was 96.3%.

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A method for preparing an enriched α-tocopherol composition comprising:
   i. providing a tocopherol-containing mixture wherein α-tocopherol is present,
   ii. placing the tocopherol-containing mixture onto a separatory column containing a polyvinyl pyridine resin,
   iii. eluting tocopherols by washing the column with an organic solvent followed by an alcohol,
   iv. collecting the eluate in fractions,
   v. combining the fractions containing tocopherols, and
   vi. concentrating the combined fractions to prepare a purified tocopherol composition enriched in α-tocopherol.

2. The method of claim 1, wherein said purified tocopherol composition comprises between about 90 to 100% α-tocopherol.

3. The method of claim 1, wherein said purified tocopherol composition comprises between about 95 to 100% α-tocopherol.

4. The method of claim 1, further comprising diluting said tocopherol-containing mixture with a first organic solvent prior to adding to the column.

5. The method of claim 4, wherein said first organic solvent is heptane or hexane.

6. The method of claim 4, wherein the ratio of said tocopherol-containing mixture to said organic solvent is between about 1:0.5 to about 1:4 by volume.

7. The method of claim 6, wherein said ratio is about 1:2.

8. The method of claim 1 or 7, wherein said organic solvent and said alcohol are added to the column at a flowrate between about 5 ml/min to 10 ml/min.

9. The method of claim 8, wherein said flowrate is between about 8 ml/min to 9 ml/min.

10. The method of claim 9, wherein said organic solvent is heptane or hexane.

11. The method of claim 10, wherein the alcohol is isopropanol or methanol.

12. The method of claim 11, wherein the purified tocopherol composition comprises between about 90 to 100% α-tocopherol.

13. The method of claim 12, wherein the purified tocopherol composition comprises between about 95 to 100% α-tocopherol.

14. The method of claim 1, wherein said polyvinyl pyridine resin is a resin comprising 2-vinylpyridine or 4-vinylpryidine moieties.

15. The method of claim 14, wherein said polyvinyl pyridine resin further comprises at least one cross-linking agent, wherein said polyvinyl pyridine resin has from between about 2% to about 25% cross-linking.

* * * * *

UNITED STATES PATENT AND TRADEMARK OFFICE
CERTIFICATE OF CORRECTION

PATENT NO. : 6,673,945 B2
DATED : January 6, 2004
INVENTOR(S) : Thomas P. Binder et al.

It is certified that error appears in the above-identified patent and that said Letters Patent is hereby corrected as shown below:

Title page,
Item [56], References Cited, U.S. PATENT DOCUMENTS, "3,402,182" reference, the name should be -- Kijima, et al. --.

Column 1,
Line 15, "(a)" should read -- ($\alpha$) --.

Column 4,
Line 10, Table for Example 3, Fraction 2 column, "methane" should read -- methanol --.

Column 5,
Line 34, "the, alpha" should read -- the alpha --.

Signed and Sealed this

Twenty-first Day of December, 2004

JON W. DUDAS
*Director of the United States Patent and Trademark Office*